(12) United States Patent
Jackson

(10) Patent No.: US 8,591,552 B2
(45) Date of Patent: Nov. 26, 2013

(54) ANTI-SPLAY MEDICAL IMPLANT CLOSURE WITH MULTI-SURFACE REMOVAL APERTURE

(76) Inventor: Roger P. Jackson, Prairie Village, KS (US)

(*) Notice: Subject to any disclaimer, the term of this patent is extended or adjusted under 35 U.S.C. 154(b) by 0 days.

(21) Appl. No.: 13/507,854

(22) Filed: Aug. 2, 2012

(65) Prior Publication Data

US 2012/0310286 A1    Dec. 6, 2012

Related U.S. Application Data

(63) Continuation of application No. 10/783,889, filed on Feb. 20, 2004, now Pat. No. 8,282,673, which is a continuation-in-part of application No. 10/236,123, filed on Sep. 6, 2002, now Pat. No. 6,726,689.

(51) Int. Cl.
*A61B 17/70* (2006.01)

(52) U.S. Cl.
USPC .......................................... 606/273; 606/264

(58) Field of Classification Search
USPC ......... 606/246, 250, 264, 265, 270–275, 278, 606/279, 301, 305; 403/362; 411/411, 378, 411/393, 416, 2, 3; 285/332.3
See application file for complete search history.

(56) References Cited

U.S. PATENT DOCUMENTS

| | | | |
|---|---|---|---|
| 791,548 A | 6/1905 | Fischer |
| 1,300,275 A | 4/1919 | Johnson |
| 1,330,673 A | 2/1920 | Anderson |
| 2,083,092 A | 1/1936 | Richer |
| 2,201,087 A | 5/1940 | Hallowell |
| 2,239,352 A | 4/1941 | Cherry |
| 2,295,314 A | 9/1942 | Whitney |
| 2,537,029 A | 8/1946 | Cambern |
| 2,445,978 A | 7/1948 | Stellin |
| 2,532,815 A | 12/1950 | Kindsvatter |
| 2,553,337 A | 5/1951 | Shafer |
| 2,778,265 A | 1/1957 | Brown |
| 2,969,250 A | 1/1959 | Kull |
| 2,877,681 A | 3/1959 | Brown |
| 2,927,332 A | 3/1960 | Moore |
| 3,143,029 A | 8/1964 | Brown |

(Continued)

FOREIGN PATENT DOCUMENTS

| | | |
|---|---|---|
| DE | 3630863 | 3/1988 |
| DE | 373809 | 5/1989 |

(Continued)

OTHER PUBLICATIONS

*Spine*, Lipcott, Williams & Wilkins, Inc., vol. 24, No. 15, p. 1495, Aug. 1999.

(Continued)

*Primary Examiner* — Pedro Philogene
*Assistant Examiner* — David Comstock
(74) *Attorney, Agent, or Firm* — John C. McMahon

(57) ABSTRACT

A convex spinal fusion interbody space device includes spaced apart superior and inferior abutment surfaces which are effectively medially convex. The peak of such convexity is displaced anteriorly of a central plane through the device. The spacer device has a height which is greater than the width of the device. The spacer device is implanted between a pair of adjacent vertebrae by insertion in a tipped-over orientation and then reoriented to an upright orientation for engagement by facing surfaces of the vertebrae. Fusion promoting bone material is packed between the vertebrae and about and within the spacer device subsequent to implantation.

7 Claims, 3 Drawing Sheets

(56) References Cited

U.S. PATENT DOCUMENTS

| | | |
|---|---|---|
| D200,217 S | 2/1965 | Curtiss |
| 3,370,341 A | 2/1968 | Allsop |
| 3,498,174 A | 3/1970 | Schuster et al. |
| 3,584,667 A | 6/1971 | Reiland |
| 3,640,416 A | 2/1972 | Temple |
| 3,812,757 A | 5/1974 | Reiland |
| 3,963,322 A | 6/1976 | Gryctko |
| 4,269,246 A | 5/1981 | Larson et al. |
| 4,373,754 A | 2/1983 | Bollfrass et al. |
| 4,492,500 A | 1/1985 | Ewing |
| 4,506,917 A | 3/1985 | Hansen Arne |
| 4,577,448 A | 3/1986 | Howorth |
| 4,600,224 A | 7/1986 | Blose |
| 4,641,636 A | 2/1987 | Cotrel |
| 4,703,954 A | 11/1987 | Ortloff et al. |
| 4,707,001 A | 11/1987 | Johnson |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,838,264 A | 6/1989 | Bremer et al. |
| 4,946,458 A | 8/1990 | Harms et al. |
| 5,005,562 A | 4/1991 | Cotrel |
| 5,022,791 A | 6/1991 | Isler |
| 5,026,373 A | 6/1991 | Ray et al. |
| 5,067,955 A | 11/1991 | Cotrel |
| 5,073,074 A | 12/1991 | Corrigan et al. |
| 5,092,635 A | 3/1992 | DeLange et al. |
| 5,129,388 A | 7/1992 | Vignaud et al. |
| 5,147,360 A | 9/1992 | Dubousset |
| 5,154,719 A | 10/1992 | Cotrel |
| 5,176,483 A | 1/1993 | Baumann et al. |
| 5,207,678 A | 5/1993 | Harms et al. |
| 5,217,497 A | 6/1993 | Mehdian |
| 5,261,907 A | 11/1993 | Vignaud et al. |
| 5,261,912 A | 11/1993 | Frigg |
| 5,282,707 A | 2/1994 | Palm |
| 5,312,404 A | 5/1994 | Asher et al. |
| 5,321,901 A | 6/1994 | Kelly |
| 5,334,203 A | 8/1994 | Wagner |
| 5,346,493 A | 9/1994 | Stahurski et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,382,248 A | 1/1995 | Jacobson et al. |
| 5,385,583 A | 1/1995 | Cotrel |
| 5,387,212 A | 2/1995 | Yuan et al. |
| 5,395,371 A | 3/1995 | Miller et al. |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,487,742 A | 1/1996 | Cotrel |
| 5,496,321 A | 3/1996 | Puno et al. |
| 5,499,892 A | 3/1996 | Reed |
| 5,507,747 A | 4/1996 | Yuan et al. |
| 5,545,165 A | 8/1996 | Biedermann et al. |
| 5,554,157 A | 9/1996 | Errico et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,591,235 A | 1/1997 | Kuslich |
| 5,601,553 A | 2/1997 | Trebing et al. |
| 5,607,304 A | 3/1997 | Bailey et al. |
| 5,607,426 A | 3/1997 | Ralph et al. |
| 5,624,442 A | 4/1997 | Mellinger et al. |
| 5,630,817 A | 5/1997 | Rokegem et al. |
| 5,641,256 A | 6/1997 | Gundy |
| 5,643,260 A | 7/1997 | Doherty |
| 5,647,873 A | 7/1997 | Errico et al. |
| 5,653,710 A | 8/1997 | Harle |
| 5,669,911 A | 9/1997 | Errico et al. |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,713,705 A | 2/1998 | Grunbichler |
| 5,716,356 A | 2/1998 | Biedermann et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,741,254 A | 4/1998 | Henry et al. |
| 5,782,833 A | 7/1998 | Haider |
| 5,797,911 A | 8/1998 | Sherman |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| D407,302 S | 3/1999 | Lawson |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,944,465 A | 8/1999 | Janitzki |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,053,917 A | 4/2000 | Sherman et al. |
| 6,056,753 A | 5/2000 | Jackson |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,139,550 A | 10/2000 | Michelson |
| 6,143,032 A | 11/2000 | Schafer et al. |
| 6,146,383 A | 11/2000 | Studer et al. |
| 6,149,533 A | 11/2000 | Finn |
| 6,183,472 B1 | 2/2001 | Lutz |
| 6,187,005 B1 | 2/2001 | Brace et al. |
| 6,193,719 B1 | 2/2001 | Gournay et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,248,105 B1 | 6/2001 | Schlapfer et al. |
| 6,254,146 B1 | 7/2001 | Church |
| 6,254,602 B1 | 7/2001 | Justis |
| 6,261,039 B1 | 7/2001 | Reed |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger |
| 6,309,391 B1 | 10/2001 | Crandall et al. |

(56) References Cited

U.S. PATENT DOCUMENTS

| | | |
|---|---|---|
| 6,315,564 B1 | 11/2001 | Levisman |
| 6,322,108 B1 | 11/2001 | Riesselmann et al. |
| 6,331,179 B1 | 12/2001 | Freid et al. |
| 6,349,794 B2 | 2/2002 | Spencer |
| 6,355,040 B1 | 3/2002 | Richelsoph et al. |
| RE37,665 E | 4/2002 | Ralph et al. |
| 6,368,321 B1 | 4/2002 | Jackson |
| 6,402,752 B2 | 6/2002 | Schaffler-Wachter et al. |
| 6,440,135 B2 | 8/2002 | Orgay et al. |
| 6,440,137 B1 | 8/2002 | Horvath et al. |
| 6,443,953 B1 | 9/2002 | Perra et al. |
| 6,451,021 B1 | 9/2002 | Ralph et al. |
| 6,454,772 B1 | 9/2002 | Jackson |
| 6,471,703 B1 | 10/2002 | Ashman |
| 6,471,705 B1 | 10/2002 | Biedermann et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,520,963 B1 | 2/2003 | McKinley |
| 6,527,804 B1 | 3/2003 | Gauchet et al. |
| 6,530,929 B1 | 3/2003 | Jusis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B1 | 4/2003 | Lieberman |
| 6,551,323 B2 | 4/2003 | Doubler et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,602,255 B1 | 8/2003 | Campbell |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,932,817 B2 | 8/2005 | Baynham et al. |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,306,606 B2 | 12/2007 | Sasing |
| 2001/0001119 A1 | 5/2001 | Lombardo |
| 2002/0026193 A1 | 2/2002 | Barker et al. |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133154 A1 | 9/2002 | Saint Martin |
| 2002/0133158 A1 | 9/2002 | Saint Martin |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023243 A1 | 1/2003 | Biedermann et al. |
| 2003/0028191 A1 | 2/2003 | Shluzas |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172032 A1 | 9/2004 | Jackson |
| 2004/0176766 A1 | 9/2004 | Shluzas |
| 2004/0186473 A1 | 9/2004 | Cournoyer et al. |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0049589 A1 | 3/2005 | Jackson |
| 2005/0055026 A1 | 3/2005 | Biedermann et al. |

(56) References Cited

U.S. PATENT DOCUMENTS

| | | |
|---|---|---|
| 2005/0070899 A1 | 3/2005 | Doubler et al. |
| 2005/0080415 A1 | 4/2005 | Keyer et al. |
| 2005/0096653 A1 | 5/2005 | Doubler |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Beidermann et al. |
| 2005/0192580 A1 | 9/2005 | Dalton |
| 2005/0203511 A1 | 9/2005 | Wilson-MacDonald et al. |
| 2005/0203516 A1 | 9/2005 | Biedermann et al. |
| 2005/0216003 A1 | 9/2005 | Beidermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Liebermann |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |

FOREIGN PATENT DOCUMENTS

| | | |
|---|---|---|
| DE | 4425392 | 11/1995 |
| DE | 19507141 | 9/1996 |
| DE | 19509331 | 9/1996 |
| DE | 29810798 | 12/1999 |
| DE | 19951145 | 5/2001 |
| EP | 195455 | 9/1986 |
| EP | 172130 | 2/1987 |
| EP | 0276153 | 7/1988 |
| EP | 276153 | 7/1988 |
| EP | 465158 | 1/1992 |
| EP | 0885598 | 12/1998 |
| EP | 1090595 | 4/2001 |
| EP | 1121902 | 8/2001 |
| EP | 1190678 | 3/2002 |
| EP | 1210914 | 6/2002 |
| EP | 1570795 | 9/2005 |
| EP | 1579816 | 9/2005 |
| EP | 1634537 | 3/2006 |
| FR | 2467312 | 4/1981 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 203508 | 9/1923 |
| GB | 2082709 | 3/1982 |
| GB | 2140523 | 11/1984 |
| GB | 9202745.8 | 4/1992 |
| GB | 2365345 | 2/2002 |
| JP | 9-504727 | 5/1997 |
| RU | 371359 | 2/1993 |
| SU | 371359 | 8/1973 |
| WO | WO 92/03100 | 5/1992 |
| WO | WO94/10927 | 5/1994 |
| WO | WO94/10944 | 5/1994 |
| WO | WO9426191 | 11/1994 |
| WO | WO95/35067 | 12/1995 |
| WO | WO96/06576 | 3/1996 |
| WO | WO96/28118 | 9/1996 |
| WO | WO97/14366 | 4/1997 |
| WO | WO98/32386 | 7/1998 |
| WO | WO01/49191 | 7/2001 |
| WO | WO02/054966 | 7/2002 |
| WO | WO03/068088 | 8/2003 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/012088 | 2/2006 |
| WO | WO2006/017616 | 2/2006 |
| WO | WO2006/028537 | 3/2006 |

OTHER PUBLICATIONS

Brochure of Tyco/Healthcare/Surgical Dynamics on Spiral Radius 90D, Publication Date: Sep. 2001, pp. 1-8.

CD Horizon M8 Multi Axial Screw Spinal System Brochure, Medtronic Sofamor Danek, no publish date.

EBI Omega 21 Brochure, EBI Spine Systems, pub. 1999.

SDRS Surgical Dynamics Rod System Brochure, Surgical Dynamics, pub. 1998-99.

Silhouette Spinal Fixation System Brochure, Sulzer Medica Spine-Tech, no publish date.

The Moss Miami 6.0mm System Advertisement, author unknown, no publish date.

The Rod Plate System Brochure, Stryker Howmedica Osteonics, pub. Oct. 1999.

The Strength of Innovation Advertisement, Blackstone Medical Inc., no publish date.

Versalok Low Back Fixation System Brochure, Wright Medical Technology, Inc., pub. 1997.

VLS System Variable Locking Screw Brochure, Interpore Cross International, 1999.

Xia Spinal System Brochure, Stryker Howmedica Osteonics, no publish date.

ANTI-SPLAY MEDICAL IMPLANT CLOSURE WITH MULTI-SURFACE REMOVAL APERTURE

CROSS REFERENCE TO RELATED APPLICATIONS

The present application is Continuation of U.S. application Ser. No. 10/783,889, filed Feb. 20, 2004 which was a continuation-in-part of U.S. application Ser. No. 10/236,123, filed Sep. 6, 2002, now U.S. Pat. No. 6,726,689, both of which are incorporated by reference herein.

BACKGROUND OF THE INVENTION

The present invention is directed to a closure for use in closing between spaced arms of a medical implant and securing a rod to the implant. In particular, the closure includes a non-circular multi-surfaced or multi-lobular internal bore for improved engagement by a complementary shaped tool for purposes of removal and an interlocking helical guide and advancement structure that prevents splaying of upper ends of walls of the implant within which the closure is placed away from an axis of rotation of the closure.

Medical implants present a number of problems to both surgeons installing implants and to engineers designing them. It is always desirable to have an implant that is strong and unlikely to fail or break during usage. It is also desirable for the implant to be as small and lightweight as possible so that it is less intrusive on the patient. These are normally conflicting goals, and often difficult to resolve.

One particular type of implant presents special problems. In particular, spinal bone screws, hooks, etc. are used in many types of back surgery for repair of injury, disease or congenital defect. For example, spinal bone screws of this type are designed to have one end that inserts threadably into a vertebra and a head at an opposite end. The head is designed to receive a rod or rod-like member in a channel in the head in which the rod is both captured and locked to prevent relative movement between the various elements subsequent to installation. The channel in the head is open ended and the rod is simply laid in the open channel. The channel is then closed with a closure member. The open headed bone screws and related devices are much easier to use and in some situations must be used instead of closed headed devices.

While open headed devices are often necessary and often preferred for usage, there is a significant problem associated with them. In particular, the open headed devices conventionally have two upstanding arms that are on opposite sides of a channel that receives the rod member. The top of the channel is closed by a closure after the rod member is placed in the channel. The closure can be of a slide in type, but such are not easy to use. Threaded nuts are sometimes used that go around the outside of the arms. Such nuts prevent splaying of the arms, but nuts substantially increase the size and profile of the implant which is not desirable. Many open headed implants are closed by plugs, bodies or closures that screw into threads between the arms, because such have a low profile. However, threaded plugs have encountered problems also in that they produce radially outward directed forces that lead to splaying or spreading of the tops of the arms or at least do not prevent splaying caused by outside forces that in turn loosen the implant. In particular, in order to lock the rod member in place, a significant force must be exerted on the relatively small plug. The tightening forces are required to provide enough torque to insure that the rod member is clamped or locked in place relative to the bone screw, so that the rod does not move axially or rotationally therein. Torques on the order of 100 inch-pounds are typical.

Because open headed implants such as bone screws, hooks and the like are relatively small, the arms that extend upwardly at the head can rotate relative to the base that holds the arms so that the tops of the arms are rotated or bent outward relatively easily by radially outward directed forces due to the application of substantial forces required to secure the rod member. Historically, early closures were simple plugs that were threaded with V-shaped threads and screwed into mating threads on the inside of each of the arms. But, as noted above, conventional V-shaped threaded plugs tend to splay or push the arms radially outward upon the application of a significant amount of torque, which ends up bending the arms sufficiently to allow the threads to loosen or disengage and the closure to fail. To counter outward directed application of forces, various engineering techniques were applied to resist the spreading forces. For example, the arms were significantly strengthened by substantially increasing the width of the arms. This had the unfortunate effect of substantially increasing the weight and the profile of the implant, which was undesirable.

The tendency of the open headed bone screw to splay is a result of the geometry or contour of the threads typically employed in such devices. In the past, most bone screw head receptacles and screw plugs have employed V-shaped threads. V-threads have leading and trailing sides oriented at angles to the screw axis. Thus, torque on the plug is translated to the bone screw head at least partially in an axial outward direction, tending to push or splay the arms of the bone screw head radially outward. This in turn spreads the internally threaded receptacle away from the thread axis so as to loosen the plug in the receptacle. The threads also have smooth or linear surfaces in a radial direction that allow slippage along the surfaces since they at best fit interferingly with respect to each other and have in the past not interlocked together. Thus, forces other than insertion forces can act to easily splay the arms since the surfaces slide rather than interlock.

The radial expansion problem of V-threads due to the radial outward component of forces applied to a V-thread has been recognized in various types of threaded joints. To overcome this problem, so-called "buttress" threadforms were developed. In a buttress thread, the trailing or thrust surface is oriented perpendicular to the thread axis, while the leading or clearance surface remains angled. This theoretically results in no radially inward or outward directed forces of a threaded receptacle in reaction to application of torque on the threaded plug. However, the linear surfaces still allow sideways slippage, if other forces are applied to the arms.

Development of threadforms proceeded from buttress threadforms which in theory have a neutral radial force effect on the screw receptacle, to reverse angled threadforms which theoretically positively draw the threads of the receptacle radially inward toward the thread axis when the plug is torqued. In a reverse angle threadform, the trailing side of the external thread is angled toward the thread axis instead of away from the thread axis, as in conventional V-threads. While buttress and reverse threadforms reduce the tendency to splay, the surfaces are not interlocking and the arms can still be bent outward by forces acting on the implant. The threads can be distorted or bent by forces exerted during installation. Therefore, while these types of threadforms are designed to not exert radial forces during installation, at most such threadforms provide an interference or frictional fit and do not positively lock the arms in place relative to the closure plug.

Furthermore, it is noted that plugs of this type that use threadforms are often cross threaded. That is, as the surgeon tries to start the threaded plug into the threaded receiver, the thread on the plug is inadvertently started in the wrong turn or pass of the thread on one arm. This problem especially occurs because the parts are very small and hard to handle. When cross threading occurs, the plug will often screw part way in the receiver and then "lock up" so that the surgeon is led to believe that the plug is tight and properly set. However, the rod is not secure relative to the bone screw or other implant and the implant fails to function properly. Therefore, it is also desirable to have a closure that resists cross threading in the receiver.

As stated above, it is desirable for medical implants to have strong and secure elements which are also very lightweight and low profile so that the overall implant impacts as little as possible upon the patient. However, strong and secure are somewhat divergent goals from the goals of lightweight and low profile. Thus, size, weight, and profile must all be taken into consideration and minimized, as much as possible, consistent with effective functioning.

In order to provide sufficient strength and friction to resist movement of the various elements once the closure plug is seated, it is necessary to apply a fairly substantial amount of torque to the closure. While some closure plugs are torqued without a head, many of the closure plugs currently in use in medical implants have a driving or installation head that breaks away from the remainder of the fastener at a preselected torque in order to assure that the closure is sufficiently torqued to provide the necessary strength and locking friction. The head is also broken away in order to assure that the closure is not over-torqued. Further, the head is typically broken away in order to provide the low profile and light weight that is desired in such closure plugs.

Because the driving head is typically broken away and because it is sometimes necessary to remove the closure after implantation and setting thereof, some mechanism must be provided in order to securely engage and remove the closure. Various structures have been provided for this purpose in prior art devices. The prior art structures have had varying degrees of success, but have typically been most effective in fasteners having a diameter that is comparatively large, such as 9 to 12 millimeters, because such larger fasteners provide greater surface and volume for engagement by removal structure of one kind or another. However, it is desirable to provide an implant closure plug with a removal mechanism which works effectively with implant elements of even smaller size.

SUMMARY OF THE INVENTION

The present invention provides a closure for use particularly with an open-headed bone implant screw to secure another implant structural member therein. The closure has a cylindrical plug, base or body and a driving or installation head that is separable from the body at a preselected torque at a breakaway region or along a breakaway line. A non-circular multi-surfaced bore or aperture extends axially through the head and into the body and is accessible subsequent to break off of the installation head to form a structure or mechanism for engagement by a removal tool of similar cross section to remove the body from the bone screw, if necessary. As used herein, the term multi-surfaced is intended to include multi-lobular or any other horizontal cross section (relative to the drawings) that is not round and that is adapted to mate with an insertion tool or removal tool, so as to provide grip or purchase to the tool while the tool rotates about an axis of rotation of the closure so as to operably install and set the closure or alternatively to remove the closure upon reverse rotation of the tool. In particular, within the body of the closure, the removal aperture is formed into a non-round multi-surfaced socket to receive a closure removal tool having a non-round cross sectional shape which is complementary to the shape of the socket. As noted above, the socket has a horizontal cross section or footprint that is non-round so that after a tool of similar cross section is placed in the aperture, an interference fit is provided when the tool is rotated, so as to rotate the body.

The multi-surfaced socket of the aperture is preferably formed by a plurality of centrally facing surfaces positioned circumferentially about a socket axis and extending generally parallel to the axis that is coaxial with an axis of rotation of the body. Such surfaces may include a plurality of planar surfaces, such as or similar to a hexagonal Allen socket, or non-planar surfaces including or similar to Torx (trademark of Textron, Inc.) or other multi-lobular shapes. A multi-lobular shape preferably includes a plurality of circumferentially spaced, centrally facing, rounded lobes separated by axial grooves or channels which receive splines of the closure removal tool. The splines of the removal tool are circumferentially spaced and separated by axially extending, rounded, outwardly facing concave grooves which are shaped to closely engage the lobes of a matingly shaped closure socket. The shapes of the closure socket and closure removal tool provide for positive, non-slip engagement of the removal tool with the closure body while avoiding the localized concentrations of stresses which can occur with other configurations of separable torque transfer arrangements.

The closure is also provided with a non-threaded guide and advancement structure for securing the closure in a receiver and locking the arms against splaying once the closure is seated in the implant. Preferably, the receiver is a rod receiving channel of an open-headed bone screw, hook or other medical implant in which the channel has an open top and is located between two spaced apart arms forming the open head of the bone screw.

The body of the closure is cylindrical and has an external guide and advancement flange extending helically about the body, relative to the body axis of rotation. The guide and advancement flange preferably has a compound, anti-splay type of contour which cooperates with complementary internal mating guide and advancement structures formed into the inner surfaces of spaced apart arms forming the open head of the bone implant screw. The flange has such a compound contour that includes an inward anti-splay surface component on the flange which faces generally inward toward the body axis. The mating guide and advancement structures of the bone screw head have a complementary contour to the body flange including outward anti-splay surface components which face outward, generally away from the body axis.

The inward anti-splay surface component is preferably formed by an enlarged region near an outer periphery of the body flange near a crest of the flange. The outward anti-splay surface components are formed near an outer periphery of the mating guide and advancement structures by enlargement thereof. The complementary anti-splay surface components of the closure and head slidably engage upon rotation and cooperate to interlock the body with the arms so as to resist splaying tendencies of the arms when the closure is strongly torqued or when other forces are applied to the various elements thereof.

In use, the closure and open-headed bone screw are used to anchor a spinal fixation member, such as a rod, by threadedly implanting the bone screw into a bone and clamping the rod within the head of the bone screw using the closure body. In order to enhance clamping engagement of the rod, the body may be provided with structural features which cut into the surface of the rod to thereby reduce the likelihood of translational or rotational movement of the rod relative to the bone screw. The body is preferably provided with a "cup point", set ring, or V-ring on a forward end of the body to cut into the surface of the rod when the body is tightly torqued into the head of the bone screw. In some embodiments, the body is also provided with a central axial point on the leading end thereof.

Objects and Advantages of the Invention

Therefore, objects of the present invention include providing an improved closure for use with an open headed bone screw; providing such a closure having a cylindrical base or body and a driving or installation head that breaks away from the body at a breakaway region to provide a low or minimized profile subsequent to installation of the closure; providing such a closure having removal structure enabling positive, non-slip engagement of the closure by a removal tool; providing such a closure having an axially extending bore that passes through the installation head; providing such a closure having a removal aperture that is multi-surfaced and forms a removal tool receiving socket including a plurality of centrally facing surfaces positioned circumferentially about an axis of rotation of the body and extending generally along the axis to form the non-round, non-slip socket to receive a removal tool having a complementary shape; providing such a closure which has such a removal aperture with a multi-lobular shape including a plurality of circumferentially spaced, centrally facing, rounded lobes separated by axial grooves or channels which receive splines of the removal tool; providing such a closure wherein the removal socket becomes fully accessible to a removal tool when the installation head breaks from the body; providing such a closure in combination with an open headed bone implant screw for use in anchoring a bone fixation structural member, such as a rod; providing such a combination in which the open headed bone screw includes a pair of spaced apart arms forming a rod receiving channel; providing such a combination including an external guide and advancement flange on the closure body and internal mating guide and advancement structures located on inner surfaces of the bone screw head which slidably mate upon rotation of the body and that interlock and cooperate to resist tendencies of the arms to splay or diverge when the closure is torqued tightly into clamping engagement with a rod positioned in the channel or when external forces are applied to the implant; providing such a combination including elements to enhance setting engagement of the closure body with a rod in the bone screw channel; providing such a combination in which a forward end of the closure body is provided with a an axially aligned point and/or peripheral cup point or V-ring to cut into the surface of the rod when the body is torqued and tightened, to resist translational and rotational movement of the rod relative to the bone screw; and providing such an anti-splay closure body with a multi-surface aperture which is economical to manufacture, which is secure and efficient in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification, include exemplary embodiments of the present invention, and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
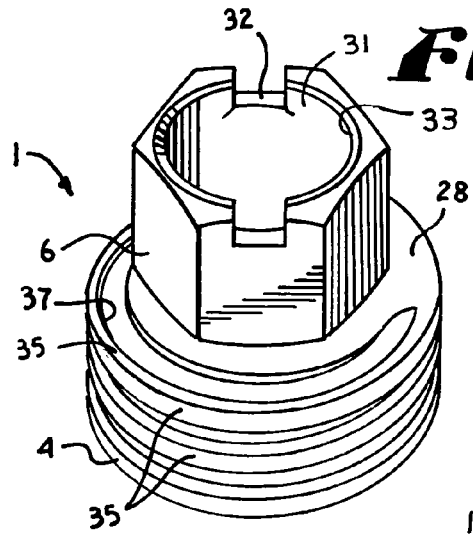
FIG. 1 is an enlarged perspective view of an anti-splay closure with a multi-surfaced removal aperture in accordance with the present invention.
Figure 2:
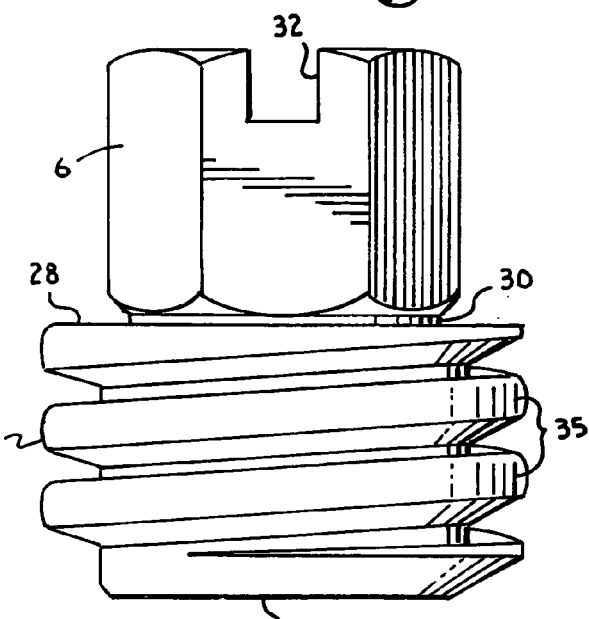
FIG. 2 is a side elevational view of the closure at a further enlarged scale.
Figure 3:
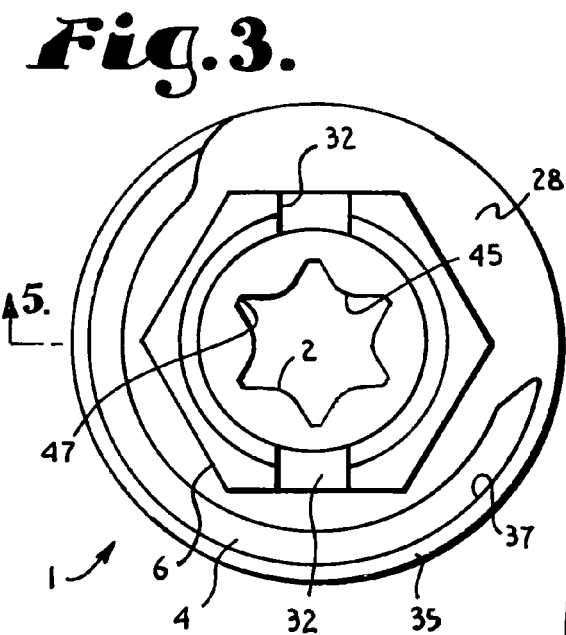
FIG. 3 is a top plan view of the closure and illustrates details of the multi-surfaced aperture of the closure with the installation head in place.
Figure 4:
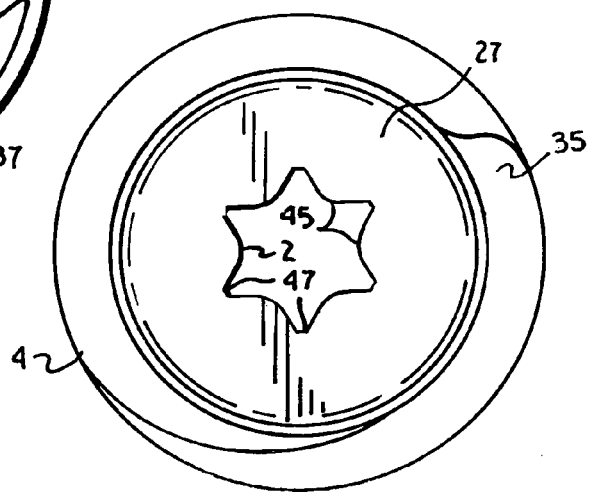
FIG. 4 is a bottom plan view of the closure and illustrates a V-ring on a forward end of the closure.
Figure 5:
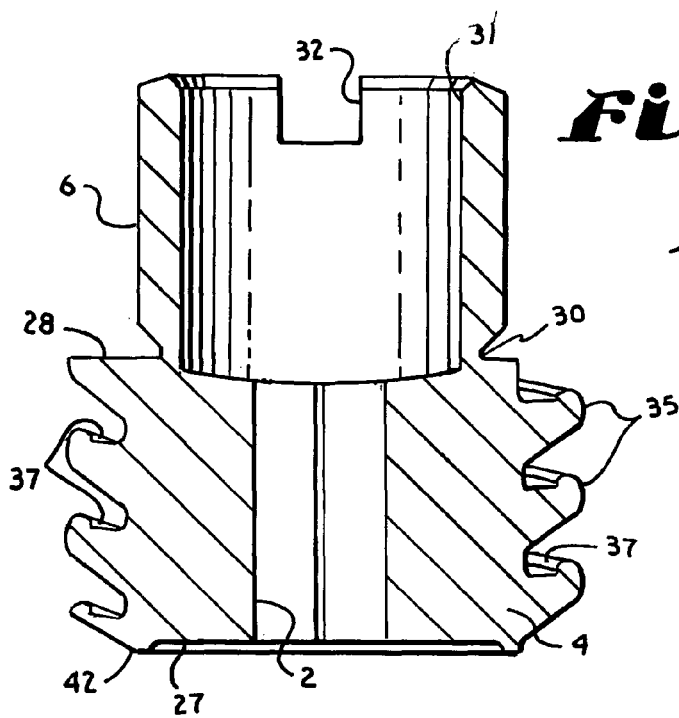
FIG. 5 is a cross sectional view of the closure, taken on line 5-5 of FIG. 3, and illustrates internal details of the multi-surfaced aperture of the closure.
Figure 6:
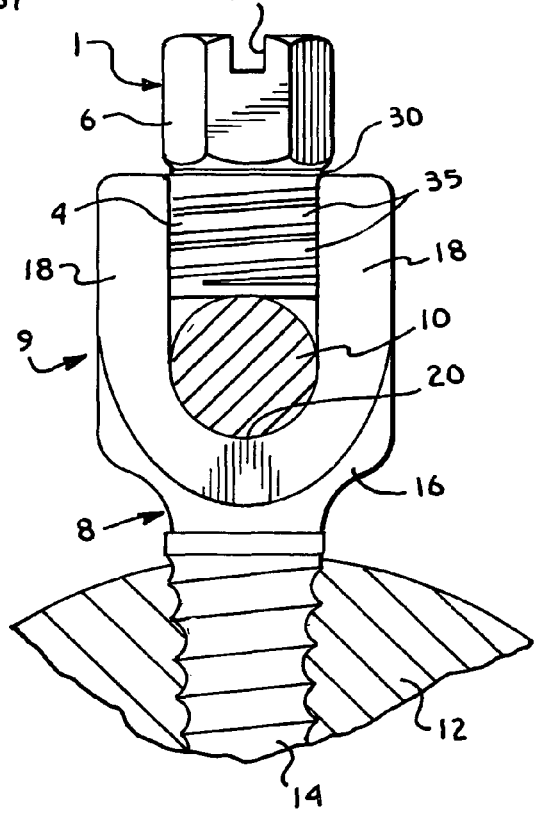
FIG. 6 is a fragmentary side elevational view at a reduced scale of the closure in combination with an open headed bone implant screw in a vertebra.

Referring to the drawings in more detail, the reference numeral 1 generally designates an anti-splay closure with a multi-surfaced aperture, such as a multi-lobular aperture 2. The closure 1 generally includes a body 4 and a breakaway installation head 6. The body 4 is used in cooperation with an open headed bone implant screw 8 (FIGS. 6 and 7) to form an implant anchor assembly 9 to secure or anchor a spinal fixation member or rod 10 with respect to a bone 12, such as a vertebra.

Figure 8:
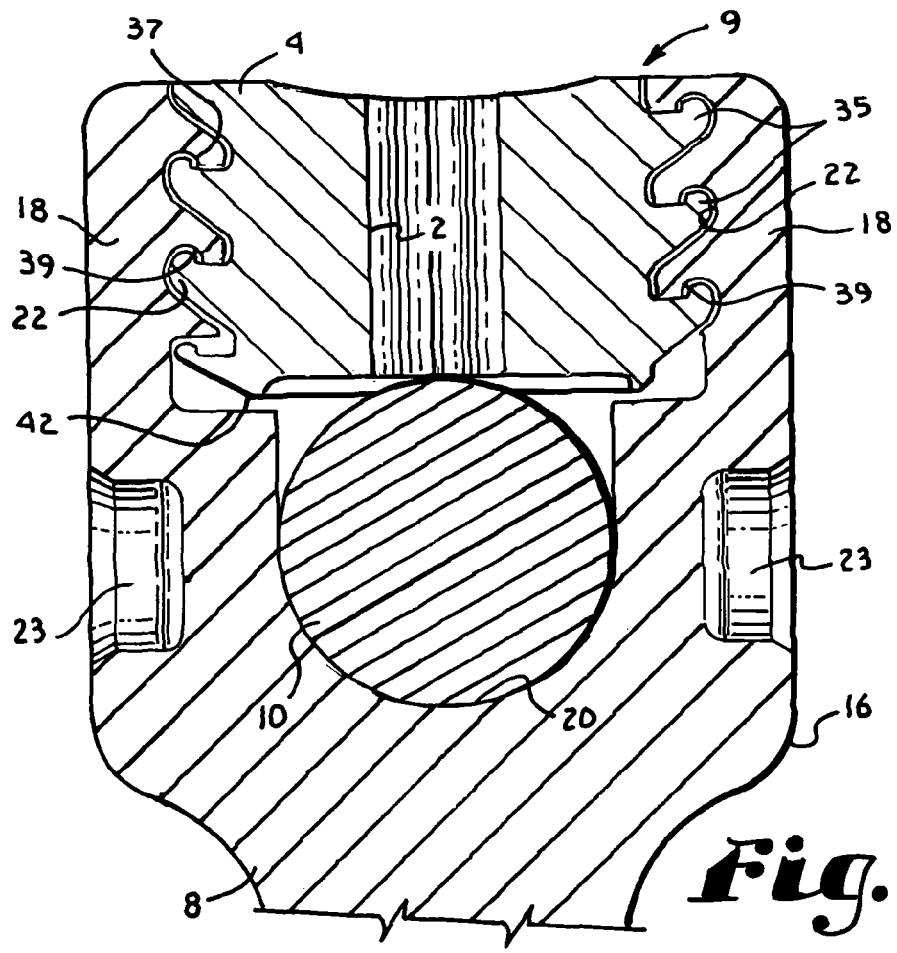
FIG. 8 is an enlarged cross sectional view of the body of the present invention positioned in clamping relationship within an open headed bone screw and illustrates details of an anti-splay guide and advancement structure of the body and bone screw head.
Figure 9:
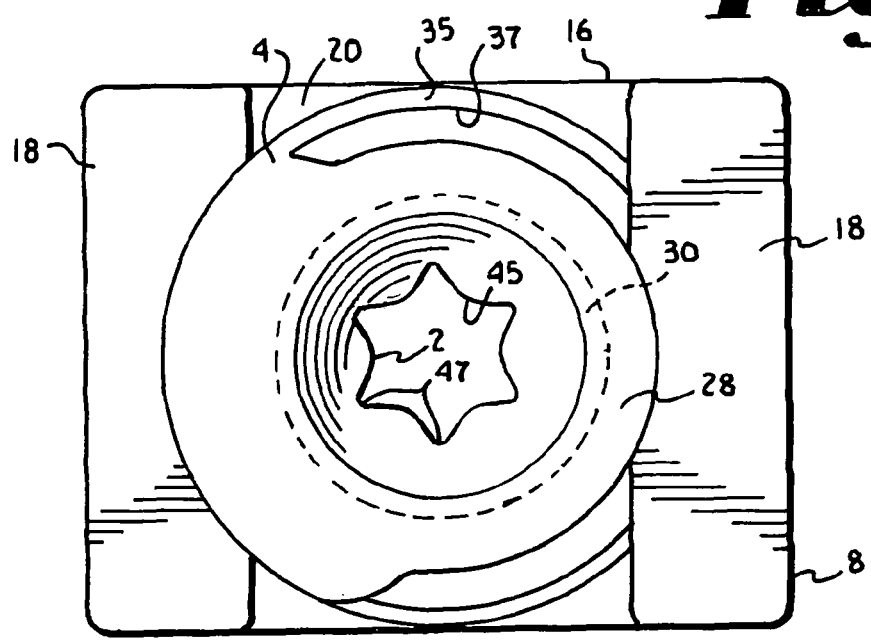
FIG. 9 is an enlarged top plan view of the closure within the open headed bone screw with the installation head removed.

The bone screw 8 includes a threaded shank 14 for threadably implanting into the bone 12 and an open head 16 formed by a pair of spaced apart arms 18 defining a U-shaped channel 20 therebetween to receive the rod 10. Inner and facing surfaces of the arms 18 have internal mating grooves or guide and advancement structures 22 (FIG. 8) tapped, or otherwise formed, therein. The head 16 has tool grip indentations 23 (FIG. 8) that allow a gripping tool (not shown) to securely hold the head 16 and facilitate gripping the bone screw 8 during manipulation for implantation of the bone screw 8 into the bone 12.

Figure 7:
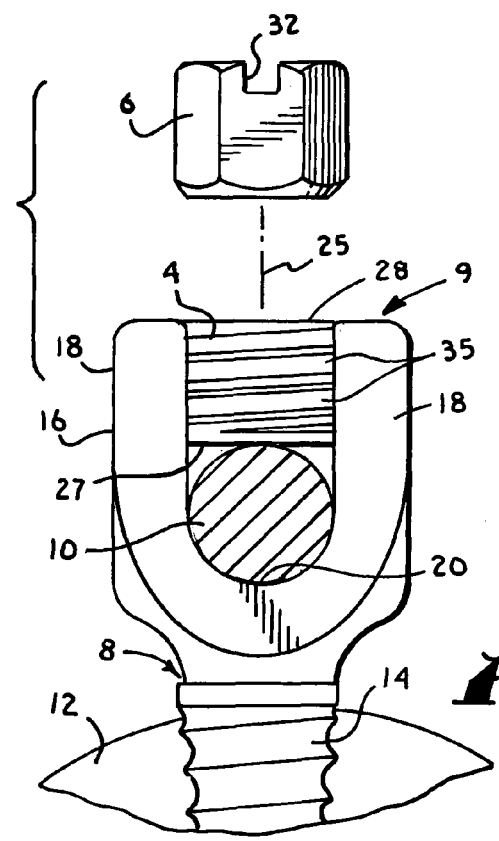
FIG. 7 is a view similar to FIG. 6 of the closure and screw and illustrates separation of the breakaway installation head from a body of the closure.

The body 4 is cylindrical in external shape about an axis of rotation 25 (FIG. 7) and has a forward, leading, or inner end 27 and a rear, trailing, or outer end 28. The breakaway head 6 is connected to the body 4 at the rear end 28 by way of a weakened breakaway line or ring 30 formed by selectively reducing the wall thickness to weaken the region. The breakaway ring 30 is thinned in such a manner that it fails at a selected relative torque between the head 6 and the body 4, as a result of torque applied to the head 6 to tighten the body 4 within the bone screw 8. As illustrated, the breakaway head 6 has a hexagonal outer shape to facilitate non-slip engagement by an installation tool (not shown) of a conventional socket type. The head 6 may also be provided with a set of tool slots 32 for alternative or more positive non-slip engagement of the head 6 by the installation tool and has a central bore 31 with an upper chamfer 33. Separation of the head 6 from the body 4, as shown in FIG. 7, is desirable to control or limit torque applied by the body 4 to the rod 10 within the bone screw head 16 and to provide a low profile joint between the body 4 and the bone screw 8.

The body 4 is provided with a guide and advancement flange 35 which extends helically about the cylindrical closure body 4. The flange 35 is enlarged near an outer periphery or radial crest thereof to form a generally inwardly facing or inward anti-splay surface 37. In a similar manner, the mating guide and advancement structures 22 are enlarged near the radially outward peripheries thereof to form generally outwardly facing or outward anti-splay surfaces 39. The anti-splay or splay resisting surfaces 37 and 39 mutually engage or slide closely relative to one another when the body 4 is rotated and thereby advanced into the bone screw head 16 so as to interlock thereby also interlocking the body 4 to the arms 18 to resist or prevent outward splaying of the arms 18 in reaction to torque or other forces.

Although particular contours of the flange 35 and mating structures 22 are shown herein, other contours of anti-splay guide and advancement flanges 35 and mating structures 22 are foreseen. Examples of such alternative configurations of anti-splay or splay resisting guide and advancement flange and mating structures are disclosed in U.S. patent application Ser. No. 10/236,123 which is now U.S. Pat. No. 6,726,689 and which is incorporated herein by reference. The flange 35 and mating structures 22 cooperate to guide and advance the body 4 into clamping engagement with the rod 10 within the channel 20 in response to clockwise rotation of the body 4.

In order to more positively secure the rod 10 within the head 16 of the bone screw 8, the body 4 is provided with a V-ring or "cup point" 42 on the inner or forward end 27 thereof. The V-ring 42 cuts into the surface of the rod 10 when the body 4 is tightly torqued into the head 16. The V-ring 42 extends about a periphery of the inner end 27 of the body 4 and, thus, provides two possible areas of engagement between the body 4 and the rod 10.

In the great majority of cases, the body 4 is torqued into engagement with the rod 10 in the bone screw 8, the installation head 6 is broken away, and the anchor assembly 9 is permanently implanted in the bone 12. However, spinal alignment geometry is complex and it is sometimes necessary to make adjustments to a spinal fixation system. Additionally, slippage or failure of spinal fixation components can occur due to injury to the patient, deterioration of bone tissue, or the like. It is also possible that an implant system using anchored rods might be used therapeutically, for example, to set a broken bone, and subsequently removed. For these reasons, implant anchor assemblies often provide structures or mechanisms for releasing an anchor assembly 9 to make such adjustments or changes in a spinal fixation system. The anchor assembly 9 of the present invention provides formations for engaging the body 4 to retract it out of the bone screw head 16 to release the rod 10 to enable adjustment of the position of the rod 10 relative to the bone screw 8.

The multi-surfaced aperture 2 is coaxially positioned relative to the body 4 axis of rotation 25 and provided for non-slip engagement by a closure removal tool (not shown) having a shape which is complementary to the shape of the aperture 2. The illustrated aperture 2 is multi-lobular and is formed by a plurality of circumferentially spaced, axially extending lobes 45 separated by intervening spline receiving grooves 47. The closure removal tool (not shown) for engagement with the aperture 2 has a shape which is complementary thereto and includes circumferentially spaced splines corresponding to the grooves 47 and removal tool grooves corresponding to the lobes 45. The aperture 2 may be of a Torx type shape which is "hexlobular" or six lobed, or other multi-lobular shape.

It is also foreseen that the multi-surfaced aperture 2 could be a simpler shape, such as a multi-faceted shape having a square, triangular, rectangular, etc. shape. Such a multi-faceted shape could include a hexagonal Allen type socket (not shown) and an appropriately shaped closure removal tool (not shown). Alternatively, other non-circular, multi-surfaced shapes are envisioned for the shape of the aperture 2; however, the axis 25 passes through the aperture 2 so as to facilitate rotation of the body 4 by a tool having a single mating projection that conforms to the aperture 2.

It is to be understood that while certain forms of the present invention have been illustrated and described herein, it is not to be limited to the specific forms or arrangement of parts described and shown.

What is claimed and desired to be secured by Letters Patent is as follows:

1. In combination a bone implant screw adapted for connection to a bone fixation structural member and a closure for setting engagement with the structural member; said closure comprising:
   (a) a substantially cylindrical body having an outer cylindrical surface relative to a central closure axis;
   (b) a substantially continuous guide and advancement flange extending helically about said outer cylindrical surface and being sized and shaped to interlock with a discontinuous mating guide and advancement flange on a receiving structure; said continuous flange having a leading surface and a trailing surface relative to a direction of forward advancement; said leading surface sloping rearwardly from said body and being free of engagement with an opposed surface of the mating guide and advancement flange; the trailing surface being compound in contour having a substantially horizontal loading surface adjacent to the body and an outward raised portion with a top surface that remains unloaded when in use.

2. The combination according to claim 1 wherein said body having a multi-surface aperture formed therein that is aligned with said closure axis and that is elongated along said closure axis, said aperture opening onto a trailing surface of said body and including a plurality of circumferentially spaced, centrally facing surfaces extending substantially parallel to said closure axis that are aligned to form a removal socket adapted to receive a removal tool.

3. The combination according to claim 1 including wherein said body having a multi-lobular aperture formed therein which is aligned on and elongated along said closure axis, said aperture including a plurality of circumferentially spaced lobes extending substantially parallel to said closure axis and said lobes circumferentially alternating with bore grooves extending substantially parallel to said closure axis to form a removal socket adapted to receive a removal tool.

4. The combination of a bone implant screw adapted for connection to a bone fixation structural member and a closure for setting engagement with the structural member; said closure comprising:
   (a) a substantially cylindrical body having an outer cylindrical surface relative to a central closure axis;
   (b) a guide and advancement flange extending helically about said outer cylindrical surface; said guide and advancement flange being sized and shaped to interlock with a mating guide and advancement flange on a receiving bone screw; said flange having a trailing surface and a leading surface relative to said forward advancement direction;
   (c) said trailing surface being compound in contour and including an inner horizontal surface and an outer raised portion with a top surface; the leading surface sloping rearwardly relative to the direction of advancement, wherein the leading surface and the top surface remain free of engagement when mated with the mating guide and advancement flange on a receiving bone screw;
   (d) a threaded shank adapted for threaded implanting into a bone; and
   (e) an open head formed by a pair of spaced apart arms having mutually facing channel surfaces defining a structural member receiving channel to receive a bone fixation structural member.

5. A combination of a bone implant screw adapted for connection to a bone fixation structural member and a closure for setting engagement with the structural member; said closure including a substantially cylindrical body having an outer cylindrical surface relative to a central closure axis, the improvement comprising:
   (a) said closure having a flange that has a leading surface and a trailing surface;
      i) the trailing surface being compound in contour so as to form:
         1) a substantially continuous guide and advancement flange extending helically about said outer surface and including an inward facing anti-splay surface component facing generally toward said closure axis; and
         2) an inner loading surface that is adjacent to the body and that is generally horizontal and an outer raised portion that has a top surface;
      ii) the leading surface slopes rearwardly from the body with respect to a direction of advancement;
   (b) said flange being sized and shaped to interlock with a mating guide and advancement flange on a receiving structure, such that the leading surface and the top surface remain free of engagement when mated with the mating guide and advancement flange on the receiving structure;
   (c) said bone screw including a threaded shank adapted for threaded implanting into a bone; and
   (d) an open head formed by a pair of spaced apart arms having mutually facing channel surfaces defining a structural member receiving channel to receive a bone fixation structural member.

6. The combination according to claim 5 wherein said body having a multi-surfaced aperture formed therein which is located and elongated along said closure axis, said aperture including a plurality of circumferentially spaced surfaces extending substantially parallel to said closure axis so as to form a removal socket adapted to receive a removal tool.

7. In combination a bone implant anchor adapted for connection to a bone fixation structural member and a closure for setting engagement with the structural member; said closure comprising:
   (a) a substantially cylindrical body having an outer cylindrical surface relative to a central closure axis;
   (b) a substantially continuous guide and advancement flange extending helically about said outer cylindrical surface and being sized and shaped to interlock with a discontinuous mating guide and advancement flange on a receiving structure of the anchor; said continuous flange having a leading surface and a trailing surface relative to a direction of forward advancement; said leading surface being free of engagement with an opposed surface of the mating guide and advancement flange; the trailing surface being compound in contour and having a linear loading surface adjacent the body and an outward raised portion with a top surface that remains unloaded when in use.

* * * * *